(12) United States Patent
Giri (10) Patent No.: US 11,246,743 B2
(45) Date of Patent: Feb. 15, 2022

(54) SYSTEM AND METHOD FOR SENSOR DRIVEN INTELLIGENT ORAL APPLIANCE

(71) Applicant: Archis Health Investments LLC, Excelsior, MN (US)

(72) Inventor: Subha Giri, Eden Prairie, MN (US)

(73) Assignee: Archis Health Investments, Excelsior, MN (US)

( * ) Notice: Subject to any disclaimer, the term of this patent is extended or adjusted under 35 U.S.C. 154(b) by 943 days.

(21) Appl. No.: 15/316,382

(22) PCT Filed: Jun. 4, 2015

(86) PCT No.: PCT/US2015/034197
§ 371 (c)(1),
(2) Date: Dec. 5, 2016

(87) PCT Pub. No.: WO2015/187949
PCT Pub. Date: Dec. 10, 2015

(65) Prior Publication Data
US 2017/0196727 A1    Jul. 13, 2017

Related U.S. Application Data

(60) Provisional application No. 62/007,593, filed on Jun. 4, 2014.

(51) Int. Cl.
*A61F 5/56* (2006.01)
*A61B 5/369* (2021.01)
(Continued)

(52) U.S. Cl.
CPC ............ *A61F 5/566* (2013.01); *A61B 5/0022* (2013.01); *A61B 5/0024* (2013.01);
(Continued)

(58) Field of Classification Search
CPC ... A61F 5/566; A61F 5/56; A61C 7/06; A61C 7/08; A61C 7/10; A61C 7/36;
(Continued)

(56) References Cited

U.S. PATENT DOCUMENTS 5,921,942 A * 7/1999 Remmers ................ A61F 5/566
                                                        600/529
2005/0081859 A1* 4/2005 Scarberry ............... A61F 5/566
                                                        128/206.29
(Continued)

FOREIGN PATENT DOCUMENTS

CA      2 774611 A1 *  2/2011
WO   WO-2007/014429 A1   2/2007
(Continued)

OTHER PUBLICATIONS

International Search Report and Written Opinion, issued by ISA/U.S. in regard to corresponding international patent application Serial No. PCT/US2015/034197; dated Sep. 8, 2015, 7 pages; USA.
Extended European Search Report, issued by the European Patent Office, regarding corresponding patent application Serial No. EP15802874.6; dated Nov. 15, 2017, 7 pages.
(Continued)

*Primary Examiner* — Camtu T Nguyen
(74) *Attorney, Agent, or Firm* — Fox Rothschild LLP (57) ABSTRACT

A system and method for improving a sleep disorder is provided. The system includes an oral appliance having a mandibular occlusal plate operably coupled to a maxillary occlusal plate, the plates molded to fit an individual's jaw; an actuator and one or more sensors in communication therewith for sensing physiologic parameters of a user, the actuator operably coupled to the maxillary occlusal plate for linearly advancing or retracting the mandibular occlusal plate based on commands received from a processing device.

19 Claims, 6 Drawing Sheets

(51) Int. Cl.
- *A61B 5/00* (2006.01)
- *A61B 5/0205* (2006.01)
- *A61B 5/024* (2006.01)
- *A61B 5/087* (2006.01)
- *A61B 5/11* (2006.01)
- *A61B 5/1455* (2006.01)

(52) U.S. Cl.
CPC .......... *A61B 5/02055* (2013.01); *A61B 5/369* (2021.01); *A61B 5/4818* (2013.01); *A61B 5/4836* (2013.01); *A61B 5/682* (2013.01); *A61B 5/024* (2013.01); *A61B 5/087* (2013.01); *A61B 5/1116* (2013.01); *A61B 5/1118* (2013.01); *A61B 5/14552* (2013.01)

(58) Field of Classification Search
CPC ... A61B 5/4542; A61B 5/4547; A61B 5/4557; A61B 5/4818; A61B 5/0022; A61B 5/024; A61B 5/02055; A61B 5/0476; A61B 5/4836; A61B 5/682; A61B 5/087; A61B 5/1116; A61B 5/1118; A61B 5/14552
See application file for complete search history.

(56) References Cited

U.S. PATENT DOCUMENTS

| | | | | |
|---|---|---|---|---|
| 2007/0235037 | A1* | 10/2007 | Thornton | A61F 5/566 128/848 |
| 2010/0316973 | A1* | 12/2010 | Remmers | A61F 5/566 433/214 |
| 2011/0071591 | A1* | 3/2011 | Bolea | A61N 1/0556 607/42 |
| 2013/0140289 | A1 | 6/2013 | Baratier et al. | |
| 2014/0134561 | A1 | 5/2014 | Smith et al. | |

FOREIGN PATENT DOCUMENTS

| | | |
|---|---|---|
| WO | WO 2013/049751 A2 | 4/2013 |
| WO | WO-2013/102095 A1 | 7/2013 |
| WO | WO 2013/188660 A2 | 12/2013 |

OTHER PUBLICATIONS

European Examination Report, issued by the European Patent Office, regarding corresponding patent application Serial No. 15802874.6, dated May 3, 2019, 4 pages.

* cited by examiner

SYSTEM AND METHOD FOR SENSOR DRIVEN INTELLIGENT ORAL APPLIANCE

CROSS REFERENCE TO RELATED APPLICATIONS

This application is a national stage patent application of International patent application Serial No.: PCT/US2015/034197, filed on Jun. 4, 2015; which claims the benefit of U.S. Provisional patent application Ser. No. 62/007,593, filed on Jun. 4, 2014; the entireties of which are hereby incorporated by reference.

FIELD OF THE INVENTION

The present invention relates generally to a system and method for a sensor driven intelligent oral appliance. In particular the invention relates to a system and method for a sensor driven intelligent oral appliance that is used to treat sleep disordered breathing.

BACKGROUND OF THE INVENTION

During sleep the muscles of the airway become relaxed. The relaxation of these muscles in turn reduces the diameter of the airway. Typically, the airway of a person with sleep related breathing disorders is already restricted or reduced in size, and this natural relaxation reduces the airway further. The most common sleeping disorder is obstructive sleep apnea (OSA), which is characterized by recurring collapse of the upper airway during sleep, resulting in sleep fragmentation and oxygen desaturation. OSA is defined as the occurrence of 5 or more episodes of complete (apnea) or partial (hypopnea) upper airway obstruction per hour of sleep (apnea-hypopnea index [AHI]) and is estimated to occur in around 24% of middle-aged men and 9% of women. The gold standard treatment for OSA is to pneumatically splint open the upper airway during sleep using continuous positive airway pressure (CPAP) devices. Although CPAP is highly efficacious in preventing upper airway collapse, patient acceptance, tolerance, and adherence is often low, thereby reducing effectiveness. Therefore, there is a significant need for effective alternative treatments.

Oral appliances have emerged as an alternative to CPAP for OSA treatment. Oral appliances are designed to improve upper airway configuration and prevent collapse through alteration of jaw and tongue position. The most common mechanism of action is to hold the lower jaw in a more anterior position. These appliances are variously termed "mandibular advancement devices (MAD)," "mandibular advancement splints (MAS)," or mandibular repositioning appliances (MRA)." MAD are generally customized devices fabricated from dental casts of a patient's dentition and bite registrations by a dentist. Generally the greater the level of advancement, the better the treatment effect, although this must be balanced against potential increase in side effects (dryness, jaw pain, bite changes, etc.).

However, above 50% of maximum advancement of the jaw there is an associated increase in reported side effects. A titration approach to determine optimal level of advancement with gradual increments over time is thought to optimize treatment outcome, although no standardized titration procedure currently exists. There is also little knowledge of how often to follow-up patients on MAD treatment for device adjustment. More information about these aspects of MAD therapy could help improve long-term effectiveness and adherence. A significant advance in single-night titration methodology has occurred with the recent development of a commercially available remotely controlled mandibular protrusion device. This protrusion device connects to upper and lower dental trays containing impressions of the patient's dentition and advances the mandible by moving forward the lower tray during polysomnographic monitoring. During the sleep titration a technician manually initiates forward movement of the lower dental tray in 0.2-0.6 mm increments in response to the appearance of apnea events. The technician continues with the advancement (within the patient's predetermined range of motion) until apena events are eliminated from sleep or until the patient's maximal allowed protrusive level is reached.

Such single-night titration results in mandibular advancement that is set for the entire duration of sleep and this advancement is unaltered for the entire time-period MAD as used for treating sleep apnea.

However, sleep is a dynamic physiological phenomenon. There is significant night-night variability in duration, depth of sleep and sleep posture, all of which directly correlate with the number and severity of apnea events. Given this dynamic nature of sleep, a static MAD maintaining advanced mandibular posture for extend periods of time, could elevate the risk for side effects in the process of improving sleep quality.

For example, peer-reviewed studies have reported that the avoidance of supine positions leads to a decrease in the number and severity of obstructive episodes. In supine posture, the upper airway caliber and resistance are greater and thus, the tendency for the upper airway to collapse further is greater in the supine position compared to the lateral position. Sleep stages (REM v/s NonREM) also similarly correlate with the severity of apnea events in a night's sleep.

Accordingly, there is a need for an oral appliance that solves the aforementioned problems associated with conventional devices and methods for treating sleep related disorders. In particular there is a need for an intelligent oral appliance that results in patients having less pain and fewer complications by not having to have their jaws protrude forward unnecessarily leading to improved compliance. Continuous gathering of data may also lead to optimal management of the sleep disorder.

BRIEF SUMMARY OF THE INVENTION

The problems outlined above are addressed by the system and method for a sensor driven oral appliance device in accordance with the invention. The system monitors changes in physiological parameters in real-time and appropriately advances the mandible to treat sleep related disorders. Also, as opposed to a human technician manually titrating the device, the invention relies on a machine driven algorithm to change the position of the mandible thus ensuring a greater degree of accuracy.

The system for improving a sleep disorder in accordance with the invention includes an oral appliance having a mandibular occlusal plate operably coupled to a maxillary occlusal plate, the plates molded to fit an individual's jaw; an actuator including a motor, a gear assembly and one or more sensors in communication therewith for sensing physiologic parameters of a user, said actuator operably coupled to said maxillary occlusal plate for linearly advancing or retracting said mandibular occlusal plate; a knowledge base that provides data on a plurality of sleep disorder conditions and normative data necessary to correct said sleep disorder conditions; a processing device in operable communication with the one or more sensors and said knowledge base, the processing device configured to (a) receive said physiologic parameter measurements from the user; (b) cross reference said physiologic parameter measurements with said knowledge base to generate a cross referenced data result indicative of a presence and/or severity of a sleep disorder event; (c) calculate a determined amount of linear movement necessary to improve the sleep disorder event to return to a normative condition; (d) transmit said determined amount to said motor; and (e) cause said maxillary occlusal plate to linearly advance or retract said mandibular occlusal plate by said determined amount to improve said sleep disorder.

A method for improving a sleep disorder is also provided. The method includes providing an oral appliance including a mandibular occlusal plate operably coupled to a maxillary occlusal plate, said plates molded to fit an individual's jaw; providing an actuator including a motor, a gear assembly and one or more sensors in communication therewith for sensing physiologic parameters of a user, said actuator operably coupled to said maxillary occlusal plate for linearly advancing or retracting said mandibular occlusal plate; providing a knowledge base that provides data on a plurality of sleep disorder conditions and normative data necessary to correct or improve said sleep disorder conditions; providing a processing device in operable communication with said one or more sensors and said knowledge base, said processing device configured to (a) receive said physiologic parameter measurements from said one or more sensors; (b) cross reference said physiologic parameter measurements with said knowledge base to generate a cross referenced data result indicative of a presence and/or severity of a sleep disorder event; (c) calculate a determined amount of linear movement necessary to correct the sleep disorder event to return to a normative condition; (d) transmit said determined amount to said motor; and (e) cause said maxillary occlusal plate to linearly advance or retract said mandibular occlusal plate by said determined amount to correct said sleep disorder.

BRIEF DESCRIPTION OF THE DRAWINGS

For a better understanding of the invention, and to show how the same may be carried into effect, reference will now be made, by way of example, to the accompanying drawings, in which.

DETAILED DESCRIPTION OF THE INVENTION

Figure 1:
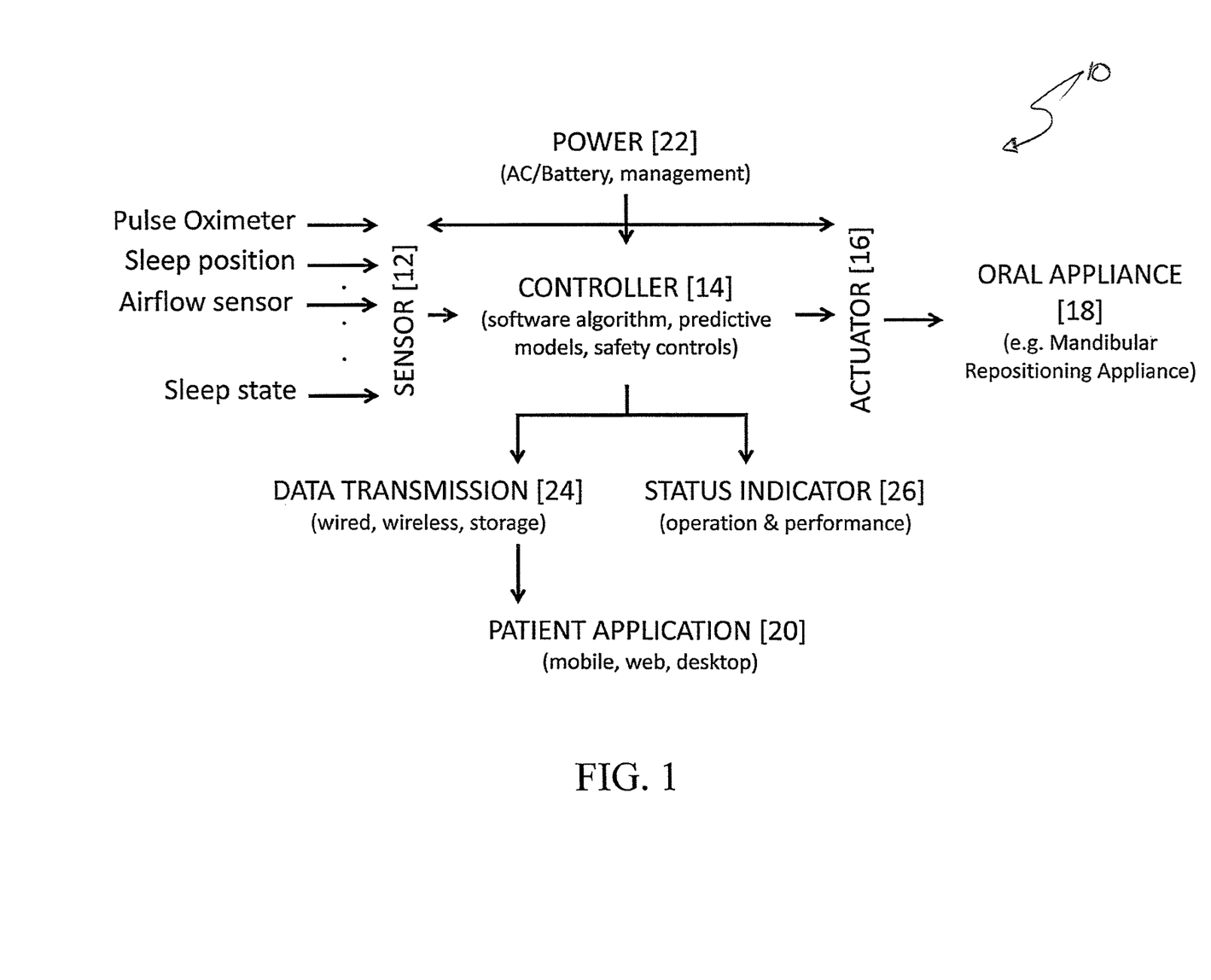
FIG. 1 is a schematic of the system in accordance with the invention.

Referring now to FIG. 1 a schematic of the system 10 in accordance with the invention is illustrated. The system broadly includes sensor 12 for sensing various physiologic parameters during an individual's sleep state. For example sensor 12 may include a pulse oximeter that detects changes in an individual's oxygen saturation. Sensor 12 may also be a position sensor that detect whether the patient is lying in a supine or lateral position. Sensor transmits physiologic parameters collected during the sleep cycle to microprocessor or controller 14. Controller 14 is powered by a source of power 22. Those of skill in the art will appreciate that source of power 22 may include one or more batteries or may include an AC source of power.

Controller 14 includes memory including a knowledge database of sleep disorders, one or more software algorithms operable to compare the data transmitted by sensor 12 to the sleep disorder knowledge database and predict the presence and/or severity of a sleep disorder event such as apnea. Controller may also include safety controls such as maximum and minimum advancement limits. Controller 14 may be an 8-bit or 16-bit microcontroller.

Figure 2:
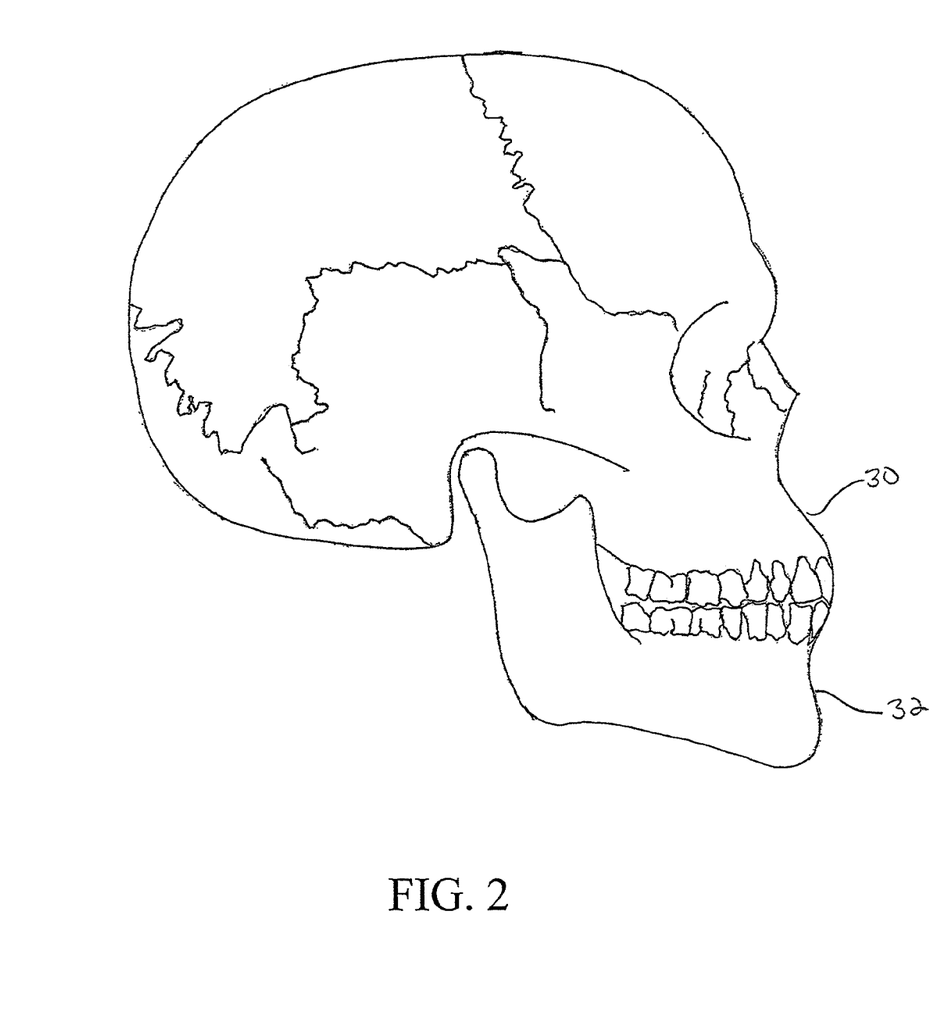
FIG. 2 is a skeletal representation of maxilla 30 and mandible 32.

Controller 14 is in operable communication with actuator 16 and transmits a signal to actuator 16 to increase or decrease the protrusion of an individual's mandible 32 (as best seen in FIG. 2) by an amount that will improve the symptoms of the sleep disorder. Actuator 16 may be a micro motor such as a DC motor, pancake, stepper, servo or piezo motor. Actuator 16 may comprise two actuators, one each for the left and right sides of the individual's mandible.

The system 10 may also include a patient web or desktop application 20 whereby data is transmitted (wired or wirelessly) from data transmission unit 24 to the web application 20 to provide an individual patient or their care team (dentist, sleep specialist and the like) with feedback regarding sleep disorder events on any particular night and how the oral appliance 18 responded. Alerts may be generated based on activity deemed outside the normal functioning range and shared among the patient and authorized care team members. Data may be transmitted via a wired set-up or may use wireless Bluetooth, WiFi and/or cellular means.

The system 10 in accordance with the invention may also include a status indicator, such as a display, that visually indicates the sleep patterns and/or the operation and/or performance and/or efficacy of the system 10, the oral appliance 18 or both.

Figure 3:
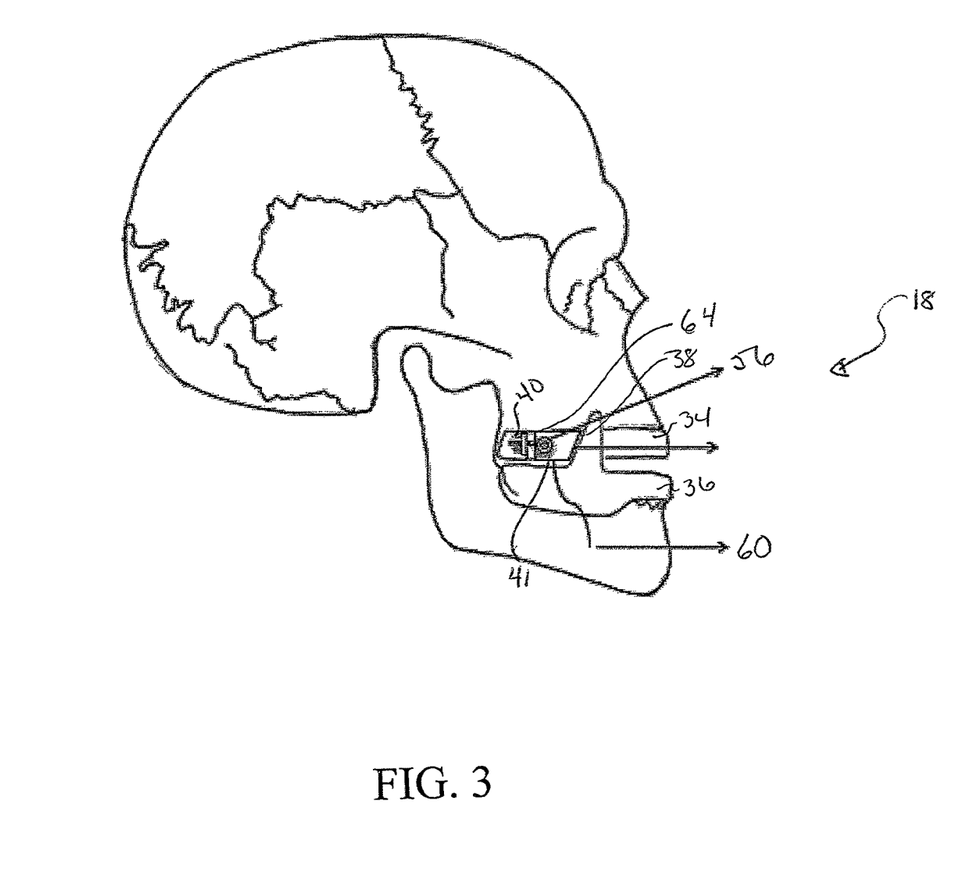
FIG. 3 is an illustration of a bilateral screw driven oral appliance in accordance with one aspect of the invention.

Referring now to FIG. 3, one aspect of an intelligent oral appliance 18 in accordance with the invention is depicted. Oral appliance 18 could be custom molded or fabricated using CAD-CAM models. Oral appliance 18 includes a maxillary occlusal plate 34 that is fitted to an individual's maxillary dentition 30 and a mandibular occlusal plate 36 that is fitted to an individual's mandibular dentition. The mandibular occlusal plate 36 is structured to engage the maxillary occlusal plate via connector 38. Connector 38 may be integrally molded with mandibular occlusal plate 36 or may be a separate piece that snap fits with mandibular occlusal plate 36. Maxillary occlusal plate 34 includes a bilateral advancement screw 40 operably coupled thereto. Bilateral advancement screw 40 includes motor 56 which may comprise a DC, pancake, stepper, servo or piezo motor. Bilateral advancement screw 40 includes electronics 58, such as a motor drive and one or more sensors to sense position, airflow and the like, that are structured to transmit data to controller 14 and receive commands from controller 14 to impart different amounts of mandibular advancement to the mandibular occlusal plate 36. Controller 14 may also be connected to additional sensors such as pulse oximeter, EEG and the like to sense related physiological parameters. Those of skill in the art will appreciate that one or more sensors may be embedded in the motor drive board while other sensors (including EEG, plus oximeter) may be attached via connectors/cables to the controller which then communicates with the motor. Upon receiving data from the sensors, the controller 14 compares the data to knowledge base stored in memory to determine the amount of movement required to improve the sleep disorder. Controller 14 then sends a signal to motor 56 to moveably advance or retract by the determined amount. If the command is to advance, screw 40 is driven by motor 56 to push against connector 38 which in turn moves the mandibular occlusal plate 36 forward by the determined amount. If the command is to retract, motor 56 drives screw 40 backwards which releases the force against connector 38 which allows the mandibular occlusal plate 36 to retract and move backwards. Those of skill in the art will appreciate that bilateral advancement screw 40 includes a counterpart screw on the opposite side of the maxillary occlusal plate 34. As seen the screw advancement device is coupled to via cable 60 to controller 14 and source of power 22

Figure 4:
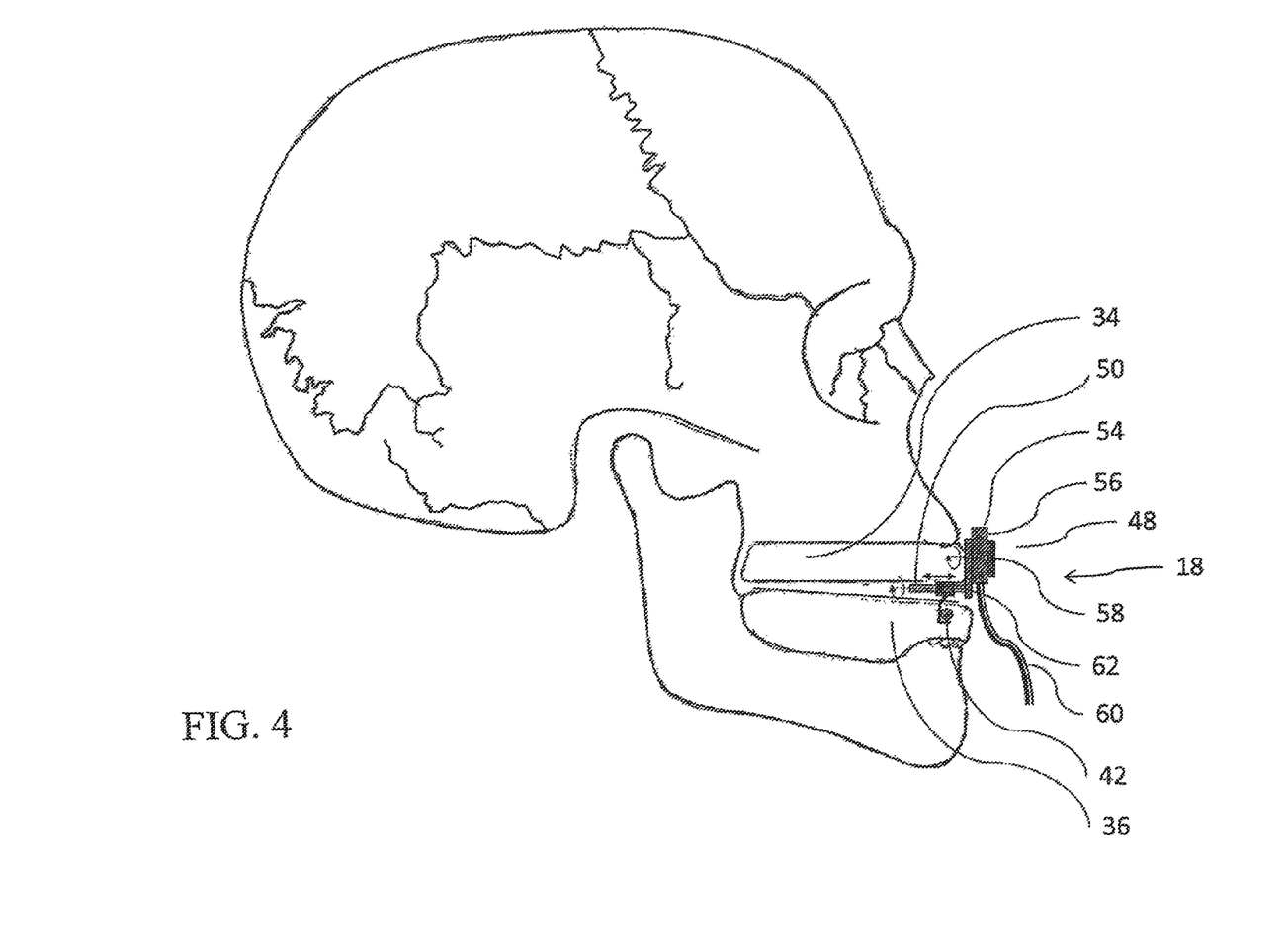
FIG. 4 is an illustration depicting another aspect of the invention using a front screw driven oral appliance.

Referring now to FIG. 4 another aspect of an intelligent oral appliance 18 is depicted. Like pieces are numbered with like numerals. Oral appliance 18 includes a maxillary occlusal plate 34 that is fitted to an individual's maxillary dentition 30 and a mandibular occlusal plate 36 that is fitted to an individual's mandibular dentition 32. Oral applicance 18 includes a front screw driven device 48 operably coupled to the maxillary occlusal plate 34. Front screw driven device 48 includes a rotating screw shaft 50, a gear 54 operably coupling the screw shaft 50 to a motor 56. Those of skill in the art will appreciate that motor 56 may comprise a DC, pancake, stepper, servo or piezo motor. Front screw driven device 48 also includes electronics 58, such as a motor drive, and one or more sensors to sense oxygen saturation, EEG, sleep position, airflow and the like that are structured to transmit data to controller 14 and receive commands from controller 14. Those of skill in the art will appreciate that one or more sensors may be embedded in the motor drive board while other sensors (including EEG, plus oximeter) may be attached via connectors/cables to the controller which then communicates with the motor.

The mandibular occlusal plate 36 includes a receptacle 42 such as a lingual bar or lingual slot that traverses left and right sides of the mandibular occlusal plate 36. In the case of a lingual bar 42, it may be integrally molded with mandibular occlusal plate 36 or may be a separate piece that snap fits with mandibular occlusal plate 36. Maxillary occlusal plate 34 includes a front advancement screw 44 operably coupled thereto. Front advancement screw 44 includes a mating piece 62 that is structured to engage receptacle 42. Mating piece 62 may comprise a hook or clasp. Hook or clasp 62 is operably coupled to the rotating screw shaft and receives commands through electronics to moveably advance or retract which in turn causes advancement and retraction of mandibular occlusal plate 36 via engagement with receptacle 42. Those of skill in the art will appreciate that the male and the female hook/clasp and receptacle/bar/slot assembly can be interchangeably positioned between the two arches so as to have the male piece in the mandibular plate and the female receptacle in the maxillary plate. Other implementations may include a ball-clasp like structures. As shown, cable 60 operably couples motor 56 and electronics 58 to controller 14. However, those of skill in the art will appreciate that controller 14 may wirelessly communicate with motor 56 and electronics 58.

Figure 5:
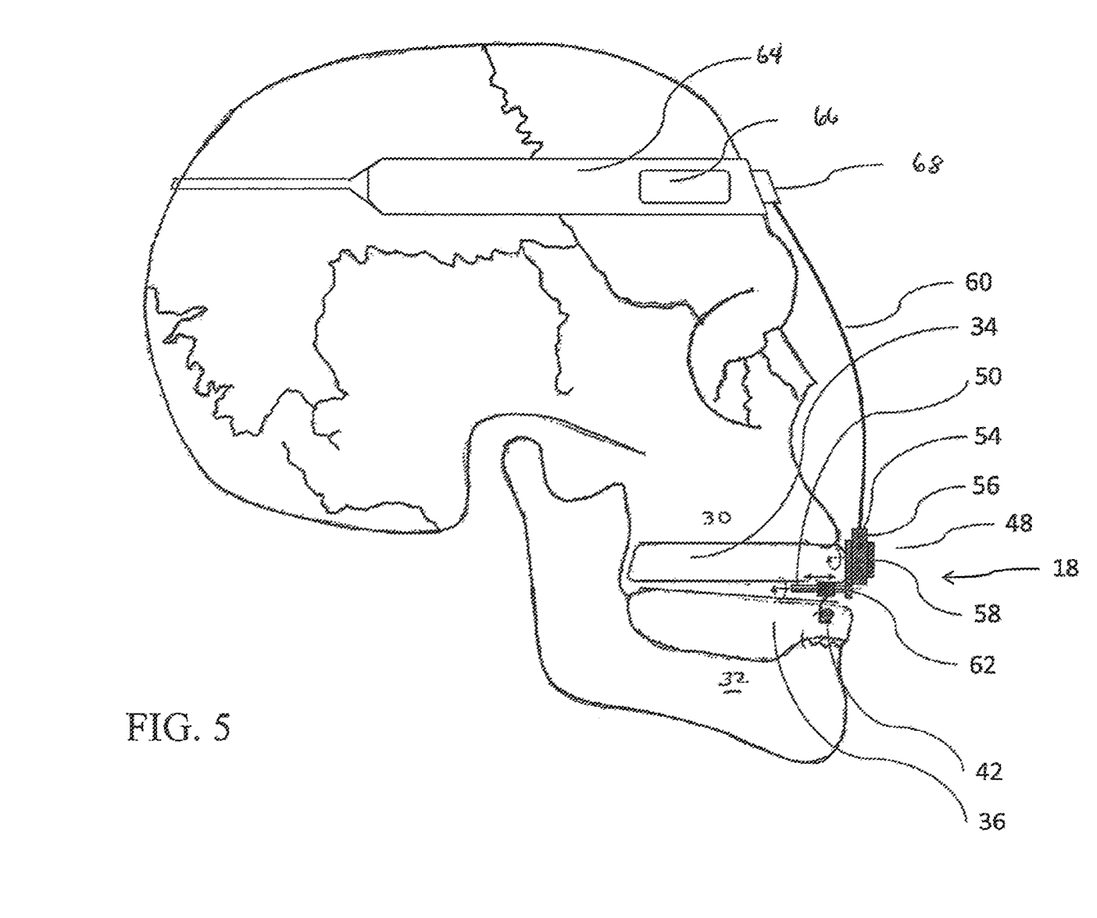
FIG. 5 is an illustration depicting the implementation of another aspect of the invention using front screw driven oral appliance utilizing a headband including an electronics board and a pulse oximeter.

Referring now to FIG. 5 an alternative aspect of the oral appliance in accordance with the invention is depicted. Like pieces are numbered with like numerals. Oral appliance 18 includes a maxillary occlusal plate 34 that is fitted to an individual's maxillary dentition 30 and a mandibular occlusal plate 36 that is fitted to an individual's mandibular dentition 32. Oral applicance 18 includes a front screw driven device 48 operably coupled to the maxillary occlusal plate 34. Front screw driven device 48 includes a rotating screw shaft 50, a gear 54 operably coupling the screw shaft 50 to a motor 56. Those of skill in the art will appreciate that motor 56 may comprise a DC, pancake, stepper, servo or piezo motor. An elastomeric or non-elastomeric headband 64 supports an electronics board 66 having a microprocessor, battery and other electronics thereon. Headband 64 also supports at least one sensor such as a pulse oximeter, body position and/or sleep position sensor. As shown, cable 60 operably couples electronics board 66, including microprocessor, with motor 56. However, those of skill in the art will appreciate that cable 60 may be eliminated and microprocessor may wirelessly communicate with motor 56. Front screw driven device 48 may also include and additional source of electronics 58, such as a motor drive, and one or more additional sensors to sense EEG, sleep position, airflow and the like that are structured to transmit data to controller 14 and receive commands from controller 14. Alternatively, all sensors may be located in the headband 64. The mandibular occlusal plate 36 includes lingual bar or lingual slot 42 that traverses left and right sides of the mandibular occlusal plate 36. If a lingual bar 42 is used, it may be integrally molded with mandibular occlusal plate 36 or may be a separate piece that snap fits with mandibular occlusal plate 36. Those of skill in the art will appreciate that a lingual slot 42 will necessarily be molded into the mandibular occlusal plate 36. Maxillary occlusal plate 34 includes a front advancement screw 44 operably coupled thereto. Front advancement screw 44 includes hook 62 that is structured to engage lingual bar 42 and that is moveably advanceable. Hook 62 is operably coupled to the rotating screw shaft and receives commands through electronics 58 or 68 to moveably advance or retract which in turn causes advancement and retraction of mandibular occlusal plate 36 via engagement with lingual bar 42.

Any of the appliances disclosed above and set forth in FIGS. 3, 4 and 5 may be used to record bruxism based on the input gathered from the controller 14. The oral appliance may also be used to alter the user's position in the event of prolonged apnea. The oral appliance for example could include an auditory or other type of alarm. For example, prolonged supping posture may lead to increased severity of the apnea and after a set threshold, the appliance may buzz or vibrate or sound an audio-visual alarm to wake and prompt the user to shift positions. In addition the web/mobile/desktop application may include a cognitive behavioral training module that is customized to the user based on the data gathered from the intelligent oral applicance.

Figure 6:
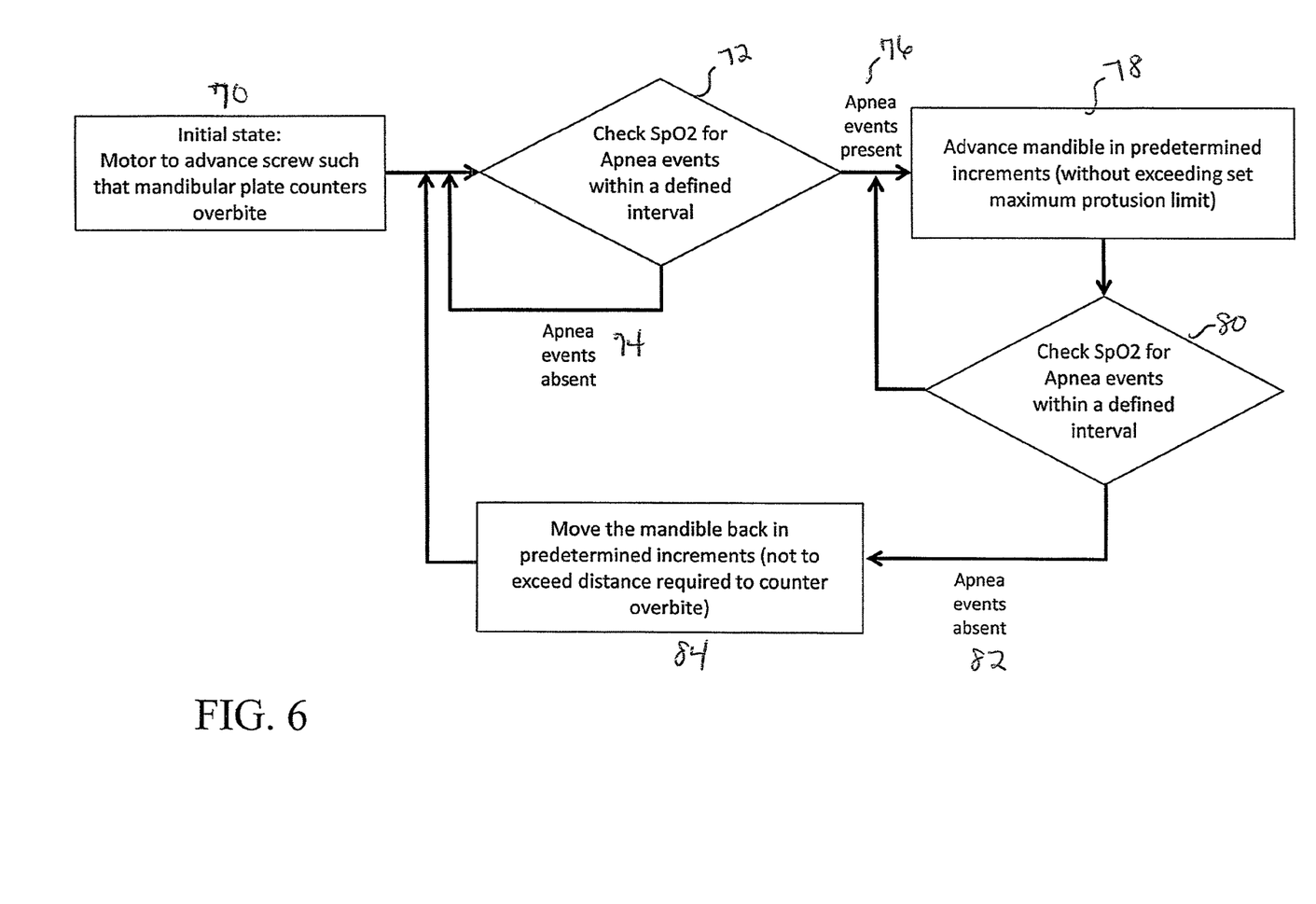
FIG. 6 is an exemplary logic flowchart generally depicting the algorithm of the system with a single sensor input in accordance with the invention.

Referring now to FIG. 6 an exemplary logic flow chart with a single sensor input is depicted. In the initial state 70 the motor 56 advance the screw 40, 44 to allow the mandibular plate 36 to counter a patient's overbite. SpO2 is checked for apena events within a defined period of time 72. If apnea events are absent the microprocessor via sensors continues to check SpO2 72. If apnea events are detected 76 the motor 56 causes the screw 40, 44 to advance the mandible in predetermined increments without exceeding a pre-determined maximum protrusion limit 78. The microprocessor continues to monitor SpO2 for apnea events 80 with a defined interval 80. If an apnea event has not been detected 82 then the microprocessor 14 transmits a command or signal to the motor to move the mandible back in predetermine increments not to exceed the distance to counter the overbite. The cycle continues with the microprocessor monitoring SpO2 for apnea events 72.

As will further be appreciated by those skilled in the art, the processes herein described may be embodied as a system, method or computer program product. Accordingly, the present invention may take the form of an entirely hardware embodiment, an entirely software embodiment (including firmware, resident software, micro-code, etc.) or an embodiment combining software and hardware aspects that may all generally be referred to as a "circuit," "module" or "system." Furthermore, the present invention may take the form of a computer program product embodied in any tangible medium of expression having computer usable program code embodied in the medium.

The processes comprising the method of the present invention have been described with reference to flow diagrams illustrating exemplary steps. It will be understood that each block of the flowchart diagrams, and combinations of blocks in the flowchart diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart diagram block or blocks.

These computer program instructions may also be stored in a computer-readable medium that can direct a computer or other programmable data processing apparatus to function in a particular manner, such that the instructions stored in the computer-readable medium produce an article of manufacture including instruction means which implement the function/act specified in the flowchart block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the flowchart diagram block or blocks.

Although the present invention has been described with reference to certain aspects and embodiments, those of ordinary skill in the art will appreciate that changes may be made in form and detail without departing from the spirit and scope of the invention.

What is claimed is:

1. A system for improving a sleep disorder comprising:
   an oral appliance including a mandibular occlusal plate operably coupled to a maxillary occlusal plate, said plates molded and configured to fit a jaw of a user;
   an actuator including a motor, a gear assembly and one or more sensors in communication therewith for sensing physiologic parameters of the user, said actuator operably coupled to said maxillary occlusal plate for linearly advancing or retracting said mandibular occlusal plate;
   a receptacle coupled to the mandibular occlusal plate and a mating piece coupled to the maxillary occlusal plate, wherein the mating piece extends between the mandibular and maxillary occlusal plates and is configured to operably engage the receptacle;
   a memory configured to store data on a plurality of sleep disorder conditions and normative data necessary to correct said sleep disorder conditions; and
   a processing device in operable communication with said one or more sensors and said memory, said processing device configured to (a) receive said physiologic parameter measurements from said one or more sensors, (b) operate an algorithm configured to cross reference said physiologic parameter measurements with said data stored in the memory to generate a cross referenced data result predictive of a presence of a sleep disorder event, (c) calculate a determined amount of linear movement necessary to improve the sleep disorder event to return to a normative condition, (d) transmit said determined movement amount to said motor, and (e) cause said maxillary occlusal plate to linearly advance or retract said mandibular occlusal plate by said determined movement amount to improve said sleep disorder.

2. The system of claim 1 wherein said one or more sensors are selected from pulse oximeter, body position, sleep position, heart rate, airflow, EEG, actigraphy and temperature sensors.

3. The system of claim 1 wherein said processing device communicates with said motor wirelessly.

4. The system of claim 1 wherein said physiologic parameters of the user include a stage of sleep of the user.

5. The system of claim 4 wherein the stage of sleep of the user includes REM or non-REM sleep.

6. The system of claim 1 wherein said physiologic parameters of the user include oxygen saturation.

7. The system of claim 1 wherein said receptacle is a lingual bar or lingual slot positioned in said mandibular occlusal plate and said mating piece is a hook or clasp coupled to said maxillary occlusal plate, said hook or clasp for operably engaging said lingual bar or lingual slot.

8. The system of claim 1 further comprising a mobile, web or desktop application for displaying information regarding physiologic parameters sensed by said one or more sensors.

9. The system of claim 1 further comprising a status indicator for indicating an operation and performance of the system.

10. The system of claim 1 further comprising a source of power for powering said processing device and said motor.

11. The system of claim 1 wherein said oral appliance is a front screw driven oral appliance.

12. The system of claim 1 wherein said processing device is further configured to cross reference said physiologic parameter measurements with said data stored in the memory to generate a cross referenced data result predictive of a severity of a sleep disorder event.

13. The system of claim 1 wherein said actuator further includes a gear assembly, said gear assembly for linearly advancing and/or retracting said mandibular occlusal plate based on commands from said processing device.

14. The system of claim 1 wherein said processing device is configured to (f) continuously monitor the physiologic parameters and advance a mandible in response to a subsequently detected apnea event.

15. The system of claim 1 wherein said one or more sensors are positioned on said oral appliance.

16. The system of claim 1 wherein said one or more sensors are positioned on a headband worn by a user, on said oral appliance or both.

17. The system of claim 1 wherein said physiologic parameters of the user include a sleep position of the user.

18. The system of claim 17 wherein the position of the user is a lateral or supine position.

19. The system of claim 1, wherein said oral appliance is a bilateral screw driven oral appliance including a first screw configured to be positioned on a right side of a jaw and a second screw configured to be positioned on a left side of the jaw.

* * * * *